United States Patent [19]

Takamoto et al.

[11] 4,048,021

[45] Sept. 13, 1977

[54] METHOD OF PURIFYING CRUDE 2,6-NAPHTHALENEDICARBOXYLIC ACID DIMETHYL ESTER

[75] Inventors: Hiromitsu Takamoto; Kiyoshi Yamamoto; Nobuo Taneda; Toru Matsubayashi; Gentaro Yamashita, all of Iwakuni, Japan

[73] Assignee: Teijin Limited, Osaka, Japan

[21] Appl. No.: 725,834

[22] Filed: Sept. 23, 1976

Related U.S. Application Data

[63] Continuation of Ser. No. 548,074, Feb. 7, 1975, abandoned.

[30] Foreign Application Priority Data

Feb. 12, 1974   Japan .................................. 49-16307

[51] Int. Cl.² ............................................. B01D 3/10
[52] U.S. Cl. ........................................ 203/91; 203/7; 560/80; 560/78
[58] Field of Search ..................... 260/475 PR, 475 B; 203/37, 6, 91, 7

[56] References Cited

U.S. PATENT DOCUMENTS

| | | | |
|---|---|---|---|
| 2,938,837 | 5/1960 | Meyer et al. | 260/475 B |
| 3,382,271 | 5/1968 | McNerney | 260/475 B |
| 3,517,053 | 6/1970 | Antonsen | 260/475 B |
| 3,639,451 | 2/1972 | Ebert | 260/475 B |
| 3,818,071 | 6/1974 | Chilton | 260/475 B |

OTHER PUBLICATIONS

Perry's Chemical Engineer's Handbook; McGraw-Hill; 4th Edition; pp. 2-87 to 2-90.

*Primary Examiner*—Frank W. Lutter
*Assistant Examiner*—Frank Sever
*Attorney, Agent, or Firm*—Sherman & Shalloway

[57] ABSTRACT

In a method of obtaining purified 2,6-naphthalenedicarboxylic acid dimethyl ester by vacuum distilling crude 2,6-naphthalenedicarboxylic acid dimethyl ester under conditions of application of heat, the improvement which comprises vacuum distilling a crude 2,6-naphthalenedicarboxylic acid dimethyl ester having an acid value ($A_f$), as expressed in milligrams of KOH required for neutralizing the carboxyl groups contained in one gram of said crude 2,6-naphthalenedicarboxylic acid dimethyl ester, of from 1.0 to 50.

4 Claims, No Drawings

METHOD OF PURIFYING CRUDE 2,6-NAPHTHALENEDICARBOXYLIC ACID DIMETHYL ESTER

This is a continuation of application Ser. No. 548,074, filed Feb. 7, 1975, now abandoned.

This invention relates to an improved method of purifying crude 2,6-naphthalenedicarboxylic acid dimethyl ester by the reduced pressure distillation of crude 2,6-naphthalenedicarboxylic acid dimethyl ester under conditions of application of heat, which method makes it possible to obtain purified 2,6-naphthalenedicarboxylic acid dimethyl ester of high grade not only in good yield and with satisfactory quality reproducibility but also operationally advantageously while preventing the formation of objectionable by-products during the performance of the distillation.

The dimethyl ester of 2,6-naphthalenedicarboxylic acid (2,6-NDA) is a useful starting compound for preparing the polyesters possessing various excellent physical properties, such, for example, as polyalkylene-2,6-naphthalenedicarboxylate. This 2,6-NDA dimethyl ester can be prepared by various methods. For instance, it can be obtained by esterifying with methanol the 2,6-NDA obtained by the oxidation of 2,6-dialkylnaphthalene or by esterifying with methanol the 2,6-NDA obtained by the heat-disproportionation and/or heat-rearrangement of naphthalenemonocarboxylic acids and/or naphthalenedicarboxylic acids other than 2,6-NDA.

The crude 2,6-NDA dimethyl ester prepared in this manner contains coloring impurities and is thus usually of yellow-brown or similar color. When such a crude 2,6-NDA dimethyl ester is used for preparing polyester, the color tone of the resulting polyester suffers. Hence, it must be removed of the coloring impurities by purification.

As the method of purification, such known unit operations as crystallization, adsorption and distillation, or combinations of these unit operations can be utilized, of which the distillation technique is to be preferred from the standpoint of operation and cost.

However, in carrying out the purification by the reduced pressure distillation of crude 2,6-NDA dimethyl ester under conditions of application of heat, there are a number of problems that need to be solved. One of the greatest of these problems is that the melting and boiling points of 2,6-NDA dimethyl ester are much higher than those of dimethyl terephthalate. Hence, it becomes necessary to conduct the distillation at higher temperatures as well as higher pressures, with the consequence that new coloring impurities and impurities, such as methyl naphthoate, resulting principally from the thermal decomposition of 2,6-NDA dimethyl ester are formed during the distillation. Because there was no simple and practical way of preventing this objectionable formation of by-products during the distillation, it was exceedingly difficult as a practical matter to obtain with quality reproducibility purified 2,6-NDA dimethyl ester of the desired high grade by means of a distillation method that would be advantageous from the standpoint of operation and cost.

As a consequence of our research with a view to developing a method by which the foregoing problem could be solved advantageously from the standpoint of the commercial operation of the method, we discovered an amazing fact. That is, when, as in the conventional methods, an esterified reaction product whose rate of esterification has been raised as high as possible is submitted to the distillation operation with the intent of raising the yield of 2,6-NDA dimethyl ester during the esterification reaction, colored matter becomes mixed in the distilled off intended 2,6-NDA dimethyl ester. However, when crude 2,6-NDA dimethyl ester whose rate of esterification is held to a somewhat lower value and of an acid value within a specified range is distilled, it was found that the intended product of high grade could be obtained with good quality reproducibility. It was also discovered that when the distillation was carried out under such conditions that the residual rate of the 2,6-NDA dimethyl ester inside the distillation zone relative to the factors of bottoms liquid phase temperature and said acid value is at least a specified value, the separation out of 2,6-NDA into the bottoms liquid phase could be prevented, thus obviating the formation of scales in the bottom of the distillation column as a result of a slurry being formed by such precipitates, with the consequence that the various adverse effects that appear such as difficulty being experienced in conducting the distillation operation, aggravation of the heat conduction, reduction in the amount of evaporation and increased heat loss could be prevented. It was further discovered that the intended product of high grade could be obtained with still better operability and quality reproducibility when the purification by distillation is carried out under conditions satisfying the foregoing specific acid value condition, and preferably under conditions satisfying both the acid value condition and the foregoing residual rate condition.

It is therefore an object of this invention to provide in a purification method of obtaining purified 2,6-NDA dimethyl ester by the reduced pressure distillation of crude 2,6-NDA dimethyl ester under application of heat, a method by which it becomes possible to obtain operationally advantageously and with good quality reproducibility purified 2,6-NDA dimethyl ester of high grade.

While the crude 2,6-NDA dimethyl ester to be used in the purification method of this invention may be that obtained by any method, usable with advantage is, for example, that obtained as previously described, by oxidizing 2,6-dialkylnaphthalene to obtain 2,6-NDA which then is methyl esterified in customary manner, or that obtained by heat-disproportionation and/or heat-rearrangement of naphthalenemonocarboxylic acids and/or naphthalenedicarboxylic acids other than 2,6-NDA to obtain 2,6-NDA which is then methyl esterified in customary manner.

The crude 2,6-NDA dimethyl ester to be submitted to distillation in the invention method is one whose acid value ($A_f$), as expressed in milligrams of KOH required for neutralizing the carboxyl groups contained in one gram of said crude ester, is 1–50, preferably 1.5–40, more preferably about 2 — about 30, and still more preferably about 3 – about 20. As shown by means of the control experiments given hereinafter, when the acid value ($A_f$) of the starting crude 2,6-NDA dimethyl ester is on the high side without the range indicated above, difficulty is experienced in preventing the objectionable formation of by-products during the distillation operation. On the other hand, if the acid value is too low, the separation of the coloring components is poor. Thus, in both instances it becomes impossible to obtain a high-grade purified 2,6-NDA dimethyl ester with good quality reproducibility and without substantial thermal decomposition to methyl naphthoate, etc., taking place. Further, as shown by means of the hereinafter given control experiments, even though the resulting purified 2,6-NDA dimethyl ester is distilled further, these coloring by-products formed during the distillation can hardly be removed, unless the acid value ($A_f$) is in the range of 1 – 50. Hence, it is practically impossible to obtain commercially advantageously a high-grade purified 2,6-NDA dimethyl ester, unless the formation of these by-products during the distillation is prevented by distilling a crude 2,6-NDA dimethyl ester satisfying the foregoing acid value ($A_f$) condition.

For obtaining the crude 2,6-NDA dimethyl ester to be used as the starting material in the invention method, the following procedure will do. In carrying out the methyl esterification of 2,6-NDA, it is carried out neither excessively nor insufficiently but appropriately so that the acid value comes within the range indicated hereinbefore by ensuring that a small amount of 2,6-NDA and/or 2,6-NDA monomethyl ester remains behind. This can be accomplished by measuring the acid value of the esterification product during the progress of the esterification reaction and stopping the reaction at the point where the desired acid value ($A_f$) is obtained. When the acid value has become too low, it may be adjusted by the addition of 2,6-NDA and/or 2,6-NDA monomethyl ester.

2,6-NDA dimethyl ester of much higher grade can be obtained by performing rectification instead of simple distillation.

The distillation can be carried out by either the continuous or batch method, but from the standpoint of operation and economy the continuous distillation method is to be preferred. The use of the conventional distilling apparatus will do. For instance, usable are the vacuum still pot, tray distillation towers, etc.

The lower limit of the distillation temperature, as indicated by the temperature of the bottoms liquid phase, is usually the melting point of 2,6-NDA dimethyl ester (about 186° C.). However, since this ester is of low volatility, it is necessary to use a high vacuum at such a low temperature. Hence, it preferably should be at least about 190° C., if possible. On the other hand, as the upper limit of the distillation temperature, as indicated by the temperature of the bottoms liquid phase, that not higher than that at which substantial decomposition of the 2,6-NDA dimethyl ester takes place will do (about 340° C.). As the decarboxylation of the foregoing ester takes place at about 300° C. and above, it is best that this upper limit be not more than about 310° C., and preferably not more than 300° C. if possible. An especially preferred distillation temperature is that in the range of about 200° to about 290° C., and particularly from about 210° to about 280° C.

In accordance with a preferred embodiment of the present invention, the aforesaid distillation is carried out in such a manner as to satisfy the following conditions: The temperature of the bottoms liquid phase of the distillation zone is maintained at from about 190° to about 340° C., and the residual rate (W/F) of said dimethyl ester in the distillation zone satisfies the following relationship (1):

$$W/F \geq 10^{\log A_f - 1/160 \cdot T_b} \quad (1)$$

wherein:
W/F is the residual rate (unit: dimensionless)

W is the rate of the withdrawal of the bottoms liquid phase (unit: Kg/hr), or the amount of the bottoms liquid phase (unit: kg), F is the rate at which the crude 2,6-NDA dimethyl ester is fed into the distillation zone (unit: kg/hr) or the amount charged of said ester (unit: kg), $A_f$ is the acid value of the crude 2,6-NDA dimethyl ester fed to the distillation zone (unit: a numerical value as indicated by the KOH mg/g of crude 2,6-NDA dimethyl ester), and $T_b$ is the temperature of the bottoms liquid phase (unit: a numerical value as indicated by ° C.); in which relationship when W is the rate of withdrawal of the bottoms liquid phase, F is the rate at which the crude 2,6-NDA dimethyl ester is fed, and when W is the amount of the bottoms liquid phase, F is the amount charged of said ester.

The upper limit of the aforesaid residual rate (W/F) is preferably about 0.9.

In carrying out the distillation, the free dicarboxylic acids and monomethyl esters contained in the crude 2,6-NDA dimethyl ester remain behind in the bottoms liquid phase as high boiling components. Hence, the liquid withdrawn from the bottom of the distillation apparatus (or the high boiling fractions) can be recycled and reused in the esterification step.

The 2,6-NDA dimethyl ester distilled and collected from the upper part of the distillation zone in accordance with the invention method can, if desired, be further purified either by submission to repeated distillation operations or by combining with other purification treatments such as recrystallization using solvents, etc.

As hereinbefore indicated, in the invention method the crude 2,6-NDA dimethyl ester having an acid value ($A_f$) of 1–50 is submitted to reduced pressure distillation under application of heat. This reduced pressure condition can be suitably varied in accordance with the heating condition and other conditions of the distillation. For example, reduced pressure conditions ranging from about 5 to about 250 mmHg abs. are most frequently employed.

While any of the crude 2,6-NDA dimethyl esters satisfying the foregoing acid value ($A_f$) condition may be used in the invention method, preferred is that which has been held after withdrawal from the esterification reaction zone at temperature conditions of 200°–300° C, preferably 220°–290° C., and more preferably 230°–280° C., for a given period of time, which varies in accordance with the foregoing temperture conditions. This holding time, i.e., the period of time from the time of withdrawal from the reaction zone to the time that the ester is to be fed to the distillation zone, can be controlled, that is by providing a storage tank at a suitable point in the line via which the reaction product is conveyed to the distillation zone. The holding temperature and holding time are preferably chosen so that they satisfy simultaneously both the following expressions $a$ and $b$.

(Holding time) × (Holding temperature − 180) > 50 ....(Expression $a$) and (Holding time) × (Holding temperature − 200) < 200 ....(Expression $b$).

More preferably the choice of the holding temperature and holding time are made to satisfy the following expressions $a'$ and $b'$.

(Holding time) × (Holding temperature − 180) > 70 ....(Expression $a'$) and (Holding time) × (Holding temperatue − 200)<180 ....(Expression b').
Still more preferably the choice of the holding temperature and holding time are made to satisfy the following expressions a" and b".
(Holding time) × (Holding temperature − 180)>100 ....(Expression a") and
(Holding time) × (Holding temperature − 200)<150 ....(Expression b").
In the foregoing expressions, the unit of time is hour, while the unit of temperature is ° C., the calculation being made by substituting these numerical values in the foregoing expressions. The holding time is as hereinbefore indicated.

According to the invention method, the coloring impurities whose removal from the crude 2,6-NDA dimethyl ester by means of the other purification methods was a difficult matter can be removed very efficiently with a simple operation, and 2,6-NDA dimethyl ester of especially excellent color can be obtained with good quality reproducibility. Further, the invention method is also effective in removing the esterification catalyst.

In addition, since no scales are formed inside the distillation column in carrying out the distillation of the crude 2,6-NDA dimethyl ester in accordance with the invention method, such difficulties as an aggravation of the heat conduction, reduction of the amount evaporated and an increase in the heat loss do not occur, with the consequence that the distillation operation can be conducted highly efficiently, and purified 2,6-NDA dimethyl ester of superior quality can be obtained in good yield with good quality reproducibility.

The following examples, along with control experiments, will be given for more fully illustrating several modes of practicing the present invention.

The degree of coloration, as used in the examples, was measured in the following manner.

A 1.0-cm-long cell is filled with a solution of 2,6-NDA dimethyl ester in o-chlorophenol at a concentration of 10 weight %. A reference cell is filled with o-chlorophenol. A spectrophotometer (Model 101 manufactured by Shimazu Seisakusho Co., Ltd., Japan) is then used, and measurement of the optical density at a wavelength of 500 micron is made. The optical density being defined by the formula:

optical density = $LOG_{10} Po/P$ where $Po$ = radiant power of incident light beam entering sample.

where $P$ = radiant power of emergent beam passing through sample. This is used to indicate the degree of coloration.

EXAMPLES 1–4 AND CONTROLS 1–5

Crude 2,6-NDA dimethyl ester having the acid value ($A_f$) shown in Table 1, below, was submitted to simple distillation at the distillation conditions shown in said Table 1. The distillation was continued until the temperature of the distillation column top could be maintained at 255° C. The results obtained are shown in Table 1, below.

Table 1

| | Starting Crude 2,6-NDA dimethyl ester | | | Distillation Conditions | | | | | | Purified 2,6-NDA dimethyl ester | |
|---|---|---|---|---|---|---|---|---|---|---|---|
| No. | Acid value ($A_f$) | Degree of coloration | Methyl naphthoate content (wt%) | Temp. of Bottoms Liquid phase (° C) | Pressure mmHg. abs | W/F | $10^{Log\ AF}$ $1/160.T_b$ | Slurry Formation | Scale Formation | Degree of Coloration | Methyl naphthoate content (wt%) |
| Control 1 | 0.7 | 1.38 | 0 | 255 | 30 | 0.3 | 0.018 | no | no | 0.14 (light yellow) | 0.01 or less |
| Control 2 | 0.8 | 1.50 | 0 | " | " | " | 0.020 | no | no | 0.17 (yellow) | 0.01 or less |
| Example 1 | 1.9 | 1.52 | 0 | " | " | " | 0.048 | no | no | 0.032 | 0.01 or less |
| Example 2 | 9.8 | 1.34 | 0 | " | " | " | 0.25 | no | no | 0.020 | 0.01 or less |
| Example 3* | 17.8 | 1.41 | 0 | " | " | 0.5 | 0.45 | no | no | 0.031 | 0.01 or less |
| Example 4 | 19 | 1.40 | 0 | " | " | " | 0.48 | no | no | 0.025 | 0.01 or less |
| Control 3 | 55 | 1.50 | 0 | " | " | " | 1.4 | yes | yes | 0.086 | 0.29 |
| Control 4 | 75 | 1.45 | 0 | " | " | " | 1.9 | yes | yes | 0.12 (light yellow) | 3.4 |
| Control 5** | 0.24 | 0.17 | 0 | " | " | 0.3 | 0.006 | no | no | 0.091 (light yellow) | 0.01 or less |

*The starting material used is one consisting of the crude 2,6-NDA dimethyl ester used in Control 2 to which has been added 0.07 weight part per part of said ester of 2,6-NDA monomethylester.
**The purified 2,6-NDA dimethyl ester obtained in control 2 was further distilled under identical distillation conditions.

EXAMPLES 5–6 AND CONTROL 6

Crude 2,6-NDA dimethyl ester having the acid value ($A_f$) shown in Table 2, below, was submitted to simple distillation at the distillation conditions shown in said Table 2. The results obtained are shown in Table 2.

Table 2

| | Starting crude 2,6-NDA dimethyl ester | | | Distillation Conditions | | | | | | Purified 2,6-NDA dimethyl ester | |
|---|---|---|---|---|---|---|---|---|---|---|---|
| No. | Acid value ($A_f$) | Degree of coloration | Methyl naphthoate content (wt%) | Temp. of Bottoms Liquid phase (° C) | Pressure mmHg. abs | W/F | $10^{log\ AF}$ $1/160.T_b$ | Slurry Formation | Scale Formation | Degree of Coloration | Methyl naphthoate content wt.% |
| Example 5 | 19 | 1.40 | 0 | 295 | 100 | 0.5 | 0.27 | no | no | 0.024 | 0.01 |
| Example 6 | 38 | 1.48 | 0 | 295 | 100 | 0.6 | 0.54 | no | no | 0.032 | 0.01 |
| Control 6 | 55 | 1.50 | 0 | 295 | 100 | 0.8 | 0.79 | no | no | 0.095 | 2.7 |

EXAMPLE 7 AND CONTROLS 7 – 8

A crude 2,6-NDA dimethyl ester identical to that used in Example 4 (acid value 19, degree of coloration 1.4, methyl naphthoate content 0%) was submitted to a continuous reduced pressure rectification at a column top pressure of 30 mmHg abs., column top temperature of 255° C., and a bottoms liquid phase temperature of 275° C., using a 10- tray distillation column. The resulting purified 2,6-NDA dimethyl ester was one whose degree of coloration was 0.015, an extremely small value. No formation during the rectification of methyl naphthoate was noted.

By way of comparison, Example 7 was repeated but using a crude 2,6-NDA dimethyl ester identical to that used in Control 4 (acid value 75, degree of coloration 1.45, methyl naphthoate content 0%). The resulting purified 2,6-NDA dimethyl ester had a degree of coloration of 0.053 (light yellow-white), and its methyl naphthoate content was 4.2%. In this case the operation of the experiment was aggravated to a marked degree, there being frequent clogging of the gas-liquid separator, vacuum lines, vacuum pump, etc.

Again, by way of comparison, the rectification was operated as in Example 7 but using the same crude 2,6-NDA dimethyl ester as that used in Control 2 (acid value 0.8, degree of coloration 1.5, methyl naphthoate content 0%). The degree of coloration of the resulting 2,6-NDA dimethyl ester was 0.15 (light yellow) in this case.

EXAMPLE 8

Crude 2,6-NDA dimethyl ester having an acid value of 4.2, a degree of coloration of 1.48 and a methyl naphthoate content of 0% was submitted to rectification by operating as in Example 7, with the result that a purified 2,6-NDA dimethyl ester having an extremely small degree of coloration of 0.017 was obtained. Further, no formation of methyl naphthoate was noted during the rectification.

EXAMPLE 9 – 12 AND CONTROLS 9–10

Crude 2,6-NDA dimethyl ester of acid value ($A_f$) of 9.2, degree of coloration of 1.35 and methyl naphthoate content of 0% was submitted to simple distillation under the distillation conditions shown in Table 3, below. The distillation was carried out such that the residual rate W/F shown in Table 3 would be obtained. The results obtained are shown in said Table 3.

content of 0% was submitted to continuous distillation under reduced pressure. The distillation apparatus used was that having a column diameter of 100 millimeters and 10 sieve trays of which the ratio of hole area was 8%. The distillation was carried out while maintaining a bottoms liquid phase portion temperature of 260° C. and so as to obtain a residual rate W/F of 0.5. The value of $10^{Log A_f \cdot 1/160 \cdot T_b}$ was 0.32. As a result of operating in this manner, the distillation could be readily carried out continuously without the formation of a slurry nor adhesion of scales. The resulting purified 2,6-NDA dimethyl ester had a low degree of coloration of 0.015, and was obtained as pure white crystals devoid of coloration. Further, the formation of methyl naphthoate by thermal decomposition was not noted.

It is claimed:

1. In a method of obtaining purified 2,6-naphthalenedicarboxylic acid dimethyl ester by vacuum distilling crude 2,6-naphthalenedicarboxylic acid dimethyl ester under conditions of application of heat, the improvement which comprises vacuum distilling in a batch or continuous operation, a crude 2,6-naphthalenedicarboxylic acid dimethyl ester having an acid value ($A_f$), as expressed in milligrams of KOH required for neutralizing the carboxyl groups contained in one gram of said crude 2,6-naphthalenedicarboxylic acid dimethyl ester, of from 1.0 to 50, at a bottom liquid phase temperature $T_b$ of from 190° C. to 340° C., and at a residual rate (W/F) of said dimethyl ester in the distillation zone which satisfies the relationship $$0.9 \geq W/F \geq 10^{(\log A_f - 1/160 \cdot T_b)} \geq 0.0075$$

wherein

W/F is the residual rate;

W is the rate of withdrawal of the bottoms liquid phase at kg/hr in the case of continuous operation, or the amount of the bottoms liquid phase in kg in the case of batch operation;

F is the rate at which the crude 2,6-naphthalenedicarboxylic acid dimethyl ester is fed into the distillation zone at kg/hr in the case of continuous operation, or the amount charged of said ester in kg in the case of batch operation;

$A_f$ is the acid value of the crude 2,6-naphthalenedicarboxylic acid dimethyl ester fed to the distillation zone at a numerical value as indicated by the KOH,mg/g of crude 2,6-naphthalenedicarboxylic acid dimethyl ester; and $T_b$ is the temperature of the bottoms liquid phase as a Table 3

| No. | Distillation Conditions ||||| Purified 2,6-NDA dimethyl ester |||
|---|---|---|---|---|---|---|---|---|
| | Temperature of Bottoms Liquid phase (° C) | Pressure mmHg.abs | W/F | $10^{Log}A_F$ $1/160 \cdot T_b$ | Slurry Formation | Scale Formation | Degree of coloration | Methyl naphthoate content (% by weight) |
| Example 9 | 210 | 8 | 0.50 | 0.45 | no | no | 0.02 | 0 |
| Example 10 | " | 8 | 0.45 | 0.45 | slight | no | 0.021 | 0 |
| Example 11 | 240 | 18 | 0.35 | 0.29 | no | no | 0.024 | 0 |
| Example 12 | 240 | 18 | 0.29 | 0.29 | slight | no | 0.025 | 0 |
| Control 9 | 210 | 8 | 0.02 | 0.039 | yes | yes | 0.19 | 0 |
| Control 10 | 240 | 18 | 0.95 | 1.74 | yes | yes | 0.052 | 0.31 |

*Crude 2,6-NDA dimethyl ester of acid value ($A_f$) of 0.8, degree of coloration of 1.5 and methyl naphthoate content of 0% used.
**Crude 2,6-NDA dimethyl ester of acid value ($A_f$) of 55, degree of coloration of 1.5 and methyl naphthoate content of 0% used.

EXAMPLE 13

Crude 2,6-NDA dimethyl ester of acid value of 13.5, degree of coloration of 1.45 and methyl naphthoate numerical value as indicated by ° C and recovering the distilled-off purified 2,6-naphthalenedicarboxylic acid dimethyl ester as distillate and removing any free dicarboxylic acids and mono-methyl esters contained in the crude 2,6-naphthalenedicarboxylic acid dimethyl ester as bottoms liquid phase; the operation of said method within the limits of said relationship being effective to substantially obviate formation of scales within the bottom of said distillation zone, so as to enable recovery of a product ester of high product reproducibility.

2. The method of claim 1 wherein said acid value is in the range 1.5–40.

3. The method of clam 1 wherein said bottoms liquid phase temperature does not exceed about 310° C.

4. The method of claim 1 which further comprises, prior to said vacuum distillation, holding said crude 2,6-naphthalenedicarboxylic acid dimethyl ester at a time and temperature which satisfy the following relationships:

(holding time) × (holding temperatue − 180) > 50
(holding time) × (holding temperature − 200) < 200 wherein the holding temperature is within the range of 200° to 300° C.

* * * * *